(12) United States Patent
Kumar et al.

(10) Patent No.: US 7,918,822 B2
(45) Date of Patent: Apr. 5, 2011

(54) SURGICAL ASPIRATION SYSTEM AND METHOD OF SURGICAL ASPIRATION

(76) Inventors: Alka Kumar, Jaipur (IN); Atul Kumar, Jaipur (IN)

( * ) Notice: Subject to any disclaimer, the term of this patent is extended or adjusted under 35 U.S.C. 154(b) by 171 days.

(21) Appl. No.: 11/844,779

(22) Filed: Aug. 24, 2007

(65) Prior Publication Data
US 2008/0051708 A1   Feb. 28, 2008

(30) Foreign Application Priority Data

Aug. 24, 2006   (IN) .............................. 1905/DEL/2006

(51) Int. Cl.
*A61M 1/00*   (2006.01)
(52) U.S. Cl. ........................................ 604/118; 604/119
(58) Field of Classification Search .................... 604/22, 604/118–121
See application file for complete search history.

(56) References Cited

U.S. PATENT DOCUMENTS

| | | | | |
|---|---|---|---|---|
| 3,890,969 A | * | 6/1975 | Fischel | 604/6.14 |
| 3,982,539 A | * | 9/1976 | Muriot | 604/120 |
| 4,395,258 A | * | 7/1983 | Wang et al. | 604/65 |
| 4,447,226 A | * | 5/1984 | Mayoral | 604/73 |
| 5,254,085 A | * | 10/1993 | Cleveland, Jr. | 604/35 |
| 5,403,276 A | * | 4/1995 | Schechter et al. | 604/22 |
| 5,656,027 A | * | 8/1997 | Ellingboe | 604/541 |
| 5,665,061 A | * | 9/1997 | Antwiler | 604/6.07 |
| 5,772,627 A | * | 6/1998 | Acosta et al. | 604/22 |
| 5,830,176 A | * | 11/1998 | Mackool | 604/22 |
| 6,283,937 B1 | | 9/2001 | Takamatsu et al. | |
| 2002/0165598 A1 | * | 11/2002 | Wahr et al. | 623/1.11 |

FOREIGN PATENT DOCUMENTS

| | | |
|---|---|---|
| EP | 0 988 865 | 3/2000 |
| EP | 0 988 865 A2 | 3/2000 |
| WO | WO 03/103747 | 12/2003 |
| WO | WO 03/103747 A1 | 12/2003 |

* cited by examiner

*Primary Examiner* — Nicholas D Lucchesi
*Assistant Examiner* — Gerald Landry, II
(74) *Attorney, Agent, or Firm* — Dickstein Shapiro LLP

(57) ABSTRACT

A single handed, safe and efficient system for aspirating a surgical site. The aspirating system of the present invention allows the surgeon to aspirate a surgical site by holding the aspiration cannula constantly in the same hand, such that the other hand of the surgeon is never needed for managing or manipulating the aspiration system in any manner. The invention allows a surgical site to be aspirated in an uninterrupted manner despite blood clots and tissue debris which constantly block the tip and the lumen of the aspiration cannula.

14 Claims, 1 Drawing Sheet

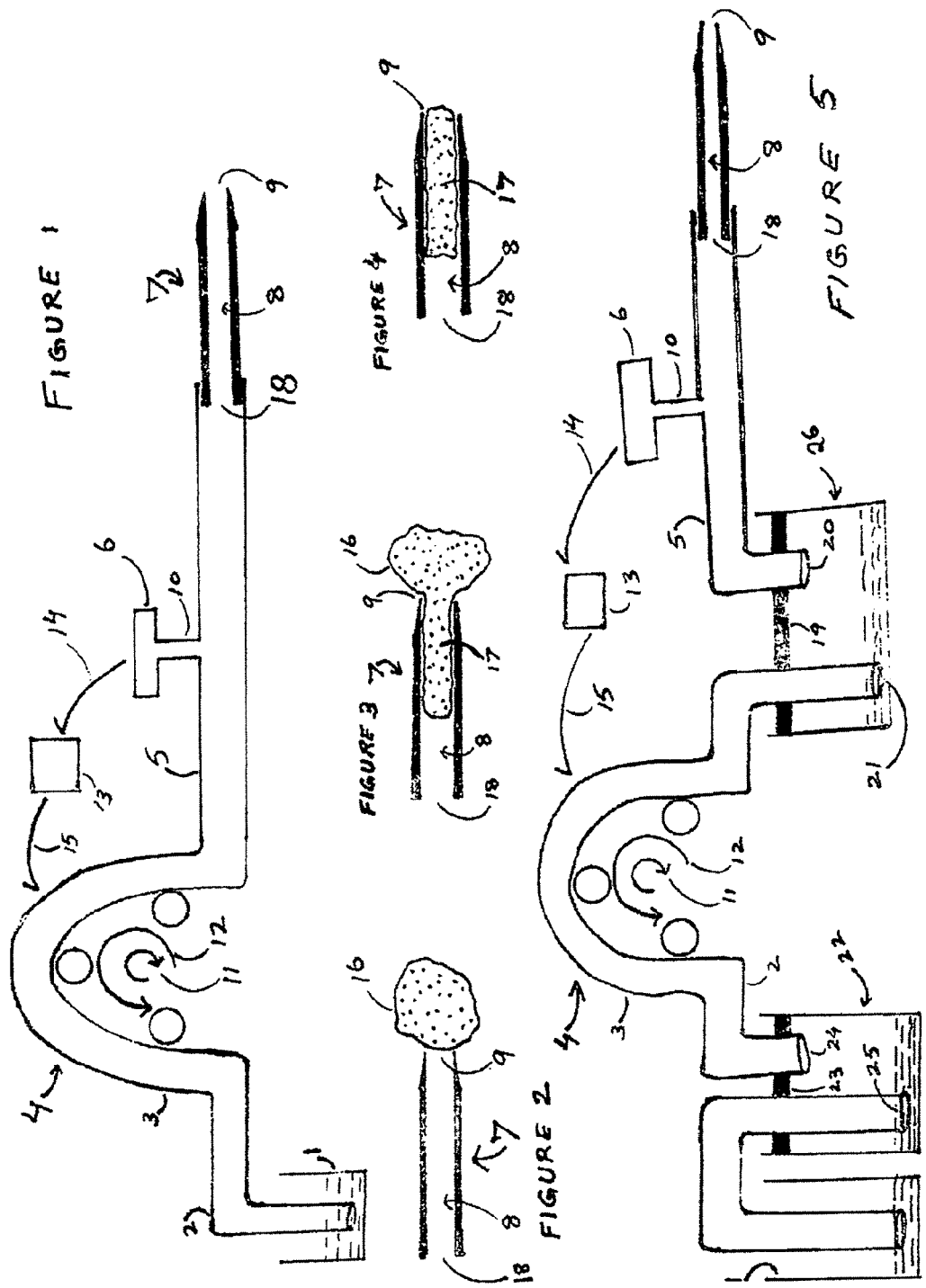

SURGICAL ASPIRATION SYSTEM AND METHOD OF SURGICAL ASPIRATION

CROSS-REFERENCE TO RELATED APPLICATIONS

The present application claims the benefit of Indian Provisional Patent Application No. 1905/DEL/2006, filed on Aug. 24, 2006, the entire disclosure of which is incorporated by reference herein.

FIELD OF THE INVENTION

The present invention relates to the field of surgery and, more particularly, to open surgical procedures, cancer surgeries and laparoscopic procedures, with special application to brain surgery.

BACKGROUND OF THE INVENTION

Some amount of bleeding is invariably associated with surgical procedures. The released blood obscures the surgeon's view by accumulating over the surgical site. In order to maintain clear vision the surgeon or an assistant intermittently aspirates the clotted and unclotted blood from the surgical site.

The prior art surgical aspiration systems generally comprise a vacuum source connected to an aspiration cannula via a suction tube. The surgeon or an assistant, while holding the aspiration cannula in one hand, bring the tip of the aspiration cannula in close proximity to the surgical site and by virtue of a negative pressure present in the suction tube the unclotted blood and the irrigation fluid is aspirated via the tip of the aspiration cannula. However, blood clots and tissue debris may block tip or the lumen of the aspiration cannula and in order to continue aspiration the surgeon attempts to dislodge the blockage by vigorously shaking the aspiration cannula. If this does not work, the suction tube is temporarily disconnected and the aspiration cannula is again shaken vigorously. If this also does not work, the surgeon mechanically dislodges the clot from the tip of the aspiration cannula by applying traction with his other free or freed hand. If the clot blocks the lumen of the aspiration cannula in a permanent like manner, then the surgeon has no choice but to detach the suction tube from the aspiration cannula and to flush the aspiration cannula in a retrograde manner under high pressure using a hypodermic syringe. Thus, the prior art surgical aspiration systems are not single handed systems because the surgeon frequently has to use his other hand in order to dislodge or to flush out the blood clots from the blocked aspiration cannula. The prior art aspiration systems also cannot function in an uninterrupted manner, because the blood clots and tissue debris which keep on blocking the tip or the lumen of the aspiration cannula have to be first dislodged or flushed before aspiration can be again resumed. The uncontrolled negative pressure created in the prior art systems can accidentally traumatize vital structures like nerves and blood vessels over the brain surface.

The present invention overcomes the disadvantages of the surgical aspirating systems of the prior art by providing a system and method for surgical aspiration which is single handed, uninterrupted, more efficient and safer than the prior art systems.

The problems associated with the existing "surgical aspiration systems" and the advantages offered by the proposed system shall now be discussed in detail in context with neurosurgical procedures like brain surgery.

BRAIN SURGERY: The brain is a very delicate organ and contains many small vital nerves and blood vessels. In brain surgery, homeostasis is mainly achieved via bipolar coagulation but even this is used very sparingly due to the fear of traumatizing vital nerves and blood vessels which could disrupt the sensory or motor functions to a vital organ. Due to extremely judicious and minimal homeostasis, brain surgery is associated with relatively more bleeding in comparison to other open surgeries. It is extremely important to maintain a constant clear vision of the brain structures and the same is achieved by a meticulously and almost continuous aspiration throughout a brain surgery procedure. In brain surgery, a lot of surgical time is wasted on account of an inefficient surgical aspiration. The aspiration related problems in brain surgery are discussed individually as follows:

Blockage of the cannula lumen: The brain is a delicate organ. Thus, neurosurgeons prefer to use miniature aspiration cannulas having inner diameters ranging between 0.3 to 3 mm. Due to the small lumen diameter, the lumen of these miniature cannulas gets easily blocked by blood clots and tissue debris. Such obstruction is permanent in nature and is relieved by disconnecting the suction tube from the cannula and then flushing the aspiration cannula retrogradely by a hypodermic surgical syringe. Many neurosurgeons like to hold the bipolar forceps in their right hand and the aspiration cannula in their left hand. In the case of a permanent like blockage of the cannula lumen, as described, the surgeon hands over the aspiration cannula to an assistant who in turn disconnects the suction tube and flushes the aspiration cannula. This wastes valuable surgical time and additional clots are also formed during this time which also need to be removed from the operative site. In the system of the proposed invention, the clot which blocks the aspiration cannula in a permanent like manner is flushed automatically with a desired time lag and the surgeon never has to hand over the cannula to an assistant for flushing. In the present invention, the clots are flushed out after a predictably desired time lag period during which time the surgeon has the option to move the tip of the cannula to a location outside the surgical field such that the blood clots are ultimately disposed well outside the operative field.

Blockage of the cannula tip: Clots also frequently superficially block only the tip and not the lumen of the aspiration cannula. In such situations, the surgeon manually dislodges the clot with his other free or freed hand which again makes surgical aspiration during brain surgery a double handed process. However, with the system of the present invention, the blood clots which superficially block the tip of the aspiration cannula do not have to be mechanically dislodged by using the other free or freed hand because such clots automatically fall away from the tip of the cannula after a predictably desired time interval during which time the surgeon again has time to move the cannula tip outside the surgical field such that the unwanted clots are disposed outside the surgical field. Such feature of the present invention not only makes surgical aspiration as a single handed maneuver but it also allows an almost uninterrupted aspiration, all of which ultimately translates into an enhanced surgical efficiency, an enhanced patient safety and a decrease in the total operating time.

Accidental trauma to brain structures: The prior art surgical aspiration systems often create uncontrolled negative pressures. In case the tip of the aspiration cannula accidentally touches a nerve or a small blood vessel, such structures may be accidentally damaged which may lead to an irreversible motor or sensory loss to important organs like the hand or leg. The present invention minimizes such accidental trauma.

The present invention has a critically vital role in brain surgery. However, the invention also finds important use in laparoscopic surgery which is described in the next paragraph.

LAPAROSCOPIC SURGERY: In operative laparoscopic procedures, blood invariably oozes from the operative site. Thus, the operative field is intermittently washed by irrigating with normal saline. However, some quantity of blood organizes in the form of clots. The irrigating fluid tends to accumulate in the dependent recesses of the posterior abdominal wall inside the inflated abdominal cavity. Such bloody irrigation fluid mixed with clots needs to be intermittently aspirated in order to maintain a clear operating field. However, the blood clots floating in the accumulated bloody irrigation fluid tend to block the tip of the aspiration cannula, and in order to relieve such blocks the surgeon either momentarily detaches the suction tube from the aspiration cannula or the surgeon vigorously shakes the tip of the aspiration cannula in order to dislodge the clot. All these maneuvers increase surgical time and can also cause surgical trauma. In brain surgery as described above and in other open surgical procedures the surgeon can use his/her other free or freed hand to dislodge a clot from the tip of the aspiration cannula, however even if the surgeon wishes, the same is not possible in laparoscopic surgery because the tip of the aspiration cannula is always located inside the distended abdominal cavity, a site which is inaccessible to the hand. In case the blood clot tends to block the lumen of the aspiration cannula in permanent like manner, then the aspiration cannula needs to be flushed as described in the previous paragraphs. The system of the present invention, when used with laparoscopic surgery, automatically flushes and also dislodges clots which intermittently block the aspiration cannula. Thus, the present invention makes surgical aspiration in laparoscopic surgery a single handed and uninterrupted process. As in brain surgery and in other open surgical procedures, in laparoscopic surgery it is not possible to dispose the non aspirated clots and other necrotic material completely outside the surgical field; at best, it is possible to temporarily park the blood clots and necrotic material from on site to another site over the posterior abdominal wall inside the inflated abdominal cavity and the present invention aids in such a maneuver as well.

Besides brain surgery and laparoscopic surgery, the present invention is useful in many other open surgical procedures as well. The use of the present invention in Caesarian Section surgery, a gynecological procedure, shall be briefly described.

CAESARIAN SECTION: In a Caesarian Section, the lower uterine body is cut with a sharp knife in order to extract the baby from the uterine cavity. Subsequent to cutting the uterine wall, a substantially large volume of amniotic fluid contained inside the fetal sac starts escaping through the uterine wall and a substantial quantity of blood which is invariably released from cut uterine wall forms large clots which tend to float in the amniotic fluid. In a Caesarian Section, the obstetrician is always in a hurry to extract the baby because any delay may cause harm to the baby and also to the mother. In order to maintain a clear operating field, the obstetrician immediately starts aspirating the blood tinged amniotic fluid but such aspiration is repeatedly interrupted by large clots which block the aspiration cannula and this may increase the time taken to extract the baby. The system of the present invention, by providing a single handed almost uninterrupted aspiration of the amniotic fluid and blood, can enhance the surgical safety for the baby as well as the mother.

The present invention also enhances the patient's safety and the surgical efficiency in extensive cancer surgeries, which are associated with substantial bleeding and in which tissue released as a result of extensive debridement needs to be removed from the surgical site.

OBJECT OF THE INVENTION

One object of the invention is to provide a single handed surgical aspiration system in which the surgeon never has to use his/her other hand to manipulate or manage the surgical aspiration system.

Another object of the invention is to provide a surgical aspiration system which aspirates in an uninterrupted manner, despite blood clots and tissue debris which intermittently block the tip and lumen of the aspiration cannula.

Another object of the invention is to provide a surgical aspiration system in which any blockage of the tip or the lumen of the aspiration cannula is relived automatically.

Another object of the invention is to provide a surgical aspiration system in which any blockage of the tip or the lumen of the aspiration cannula is relived automatically after a desired time lag.

Another object of the invention is to provide a surgical aspiration system which allows the surgeon to temporarily park blood clots and tissue debris from one location to a desired new location over the surgical site, as a single handed maneuver.

Another object of the invention is to provide a surgical aspiration system which allows the surgeon to pick up a blood clot or tissue debris by the tip of the aspiration cannula and to remove the same outside the surgical field, as a single handed maneuver utilizing only the aspiration cannula.

One further object of the invention is to provide a surgical aspiration system which minimizes tissue trauma which may otherwise occur due to the uncontrolled negative pressure inside the suction tube.

SUMMARY OF THE INVENTION

The present invention provides a method and single handed surgical aspiration system in which the surgeon can aspirate a surgical site in an uninterrupted manner, despite blood clots and tissue debris which intermittently block aspiration cannula. The system of the present invention comprises a positive displacement pump (such as a peristaltic pump) which is connected to an aspiration cannula. A pressure transducer in communication with the aspiration cannula sends pressure related information to a controller which in turn operates the pump on the basis of the pressure feedback mechanism. Whenever the lumen or the tip of the aspiration cannula is at least partially blocked by a blood clot, the pressure transducer detects a rising negative pressure which prompts the controller to operate the peristaltic pump in a reverse direction, to automatically flush out the clot from the aspiration cannula.

Other features and advantages of the present invention will become apparent from the following description of the invention which refers to the accompanying drawings.

BRIEF DESCRIPTION OF THE DRAWINGS

FIG. 1 shows the basic block diagram of the invention.

FIG. 2 shows a blood clot blocking the tip of the surgical cannula.

FIG. 3 shows a blood clot blocking the lumen of the aspiration cannula, with a part of the clot outside the tip of the surgical cannula.

FIG. 4 is similar to FIG. 3, except that a superficial part of the clot outside the tip of the aspiration cannula has been dislodged.

FIG. 5 is similar to FIG. 1, except that a proximal and a distal trap have been included.

DETAILED DESCRIPTION OF THE INVENTION

The present invention provides a system and a method of aspirating a surgical site. The system can aspirate in an interrupted manner, despite blood clots which repeatedly obstruct the tip or the lumen of the aspiration cannula The invention comprises of a pump with one end connected to a waste collecting container and its other end connected to a surgical aspiration cannula via an intervening suction tube. The pump is bi-directional in nature, meaning that it intermittently operates in opposite directions in various permutation combinations. The pump is preferably a positive displacement pump. The positive displacement pump is preferably a peristaltic pump. The pump is operated by a controller under a pressure feedback mechanism.

The basic schematic diagram of the invention is shown in FIG. 1. One end of the peristaltic pump 4 is connected to a waste collecting container 1 via a fluid drainage tube 2 whose single open end is placed near the bottom of the waste collecting container 1. For simplicity, the term "peristaltic pump 1" shall be referred to as "pump 1." Since pump 1 is bidirectional in nature, inlet or outlet ends cannot be defined with respect to pump 1. The other end of pump 1 is connected to a surgical aspiration cannula 7 via a suction tube 5. The aspiration cannula 7 is depicted by a thick black line.

A pressure transducer 6 is fluidly connected to the suction tube 5 via an intervening tube 10. The pressure transducer 6 constantly measures the pressure inside the lumen of the suction tube 5. The pressure transducer 6 may also be in the form of a membrane diaphragm incorporated in the wall of tube 5, such that the linear movement excursions of the said membrane are interpreted as pressure of the fluid inside the tube 5. The mechanical construction of the pressure transducer is not important and for simplicity the existence of tube 10 shall be continued to be considered in the rest of the manuscript. In routine surgical procedures the diameter of the inner lumen of the suction tube 5 generally ranges between about 3 to about 10 mm but it may even be smaller or greater. The diameter of the lumen 8 of the aspiration cannula 7 is generally less than the diameter of the lumen of the suction tube 5. The lumen of the aspiration cannula 7 lies between the tip 9 and the other opening 18 which connects the aspiration cannula with the suction tube 5. The rotors of the peristaltic pump 4 are denoted by three unlabeled circles. The rotors rotate and squeeze over the tube 3 of the peristaltic pump 4 thus causing flow of fluid in either direction. The direction of rotation of the bidirectional peristaltic pump 4 is depicted by two curved arrows 12 and 11. The direction of rotation of the pump 4 shall be referred to as 'direction 12' and 'direction 11' respectively. The pressure transducer 6 sends pressure related information to the controller 13 via wires 14. The controller in turn operates the pump 4 via wires 15.

When the pump 4 works in direction 12, a negative pressure is created inside the lumen of the suction of the suction tube 5. When the tip 9 of the aspiration cannula is brought in close proximity to the surgical site, then by virtue of the negative pressure, physiological fluids and unclotted blood being relatively less viscous are successfully aspirated from the surgical site via the tip 9 of the aspiration cannula. If the lumen 8 is sufficiently large, then even small blood clots are successfully aspirated without blocking the lumen 8 of the aspiration cannula 7. However, in certain procedures such as brain surgery, the aspiration cannulas are small in size having inner lumens as small as 0.3 mm. Such small lumen cannulas are blocked by even small size blood clots.

Referring to FIG. 2, by virtue of a negative pressure, a blood clot 16 denoted by a dotted area is seen blocking the tip 9 of the cannula 7 and the clot has not yet occupied any part of the lumen 8 of the aspiration cannula 7. In such situation if the negative pressure is released by temporarily disconnecting the suction tube from the aspiration cannula 7 the clot 16 could possibly fall away from the tip 9 thus releasing the block. Alternatively, the clot 16 could also be dislodged mechanically by pulling with the hand. If this clot, as described in FIG. 2, is not dislodged or if the negative pressure is increased then within a few seconds, a part of this clot can enter into the lumen 8 of the aspiration cannula 7, thus causing a permanent like block of the lumen of the aspiration cannula 7.

Referring to FIG. 3, the clot is shown to have partly entered into the lumen 8 of the cannula 7. A stem like linear mass of the clot labeled 17 is shown impacting a part of the length of the aspiration cannula and the superficial part of the clot outside the tip 9 is labeled 16.

Referring to FIG. 4, the superficial part of the clot 16 outside the lumen 8 has been dislodged and only the stem like linear part of the clot 17 is seen impacting a part of the length of the lumen 8. If the inner diameter of the lumen 8 is relatively small, as is usually the case in neurosurgical procedures related to the brain, then the stem like impacting clot 17 could cause a permanent like obstruction which may not be relieved even by increasing the magnitude of the negative pressure. In order to relieve such an obstruction the surgeon or the assistant fills sterile physiological fluid like normal saline in a hypodermic syringe, fixes the single syringe outlet to the opening 18 of the blocked aspiration cannula 7, applies pressure on the syringe piston and, in this manner, the impacted clot 17 is flushed out through the tip 9.

The present invention is useful in many surgical procedures. According to an exemplary embodiment only, the basic principles of the invention are discussed below with respect to brain surgery, assurgical aspiration is a major problem in brain surgery and the actual utility of an aspiration can be easily gauged in such surgery. In brain surgery, the surgeon generally holds the aspiration cannula in his left hand and the bipolar forceps in his right hand. The tip or the lumen of the aspiration cannula gets blocked by clots multiple times during surgery and the surgeon has to repeatedly free his/her right hand to dislodge the clot from the cannula tip. On many occasions, the cannula must be flushed, in which case the surgeon has to free both his/her hands to flush the cannula. Thus the prior art systems of surgical aspiration are not single handed and the surgeon is compelled to repeatedly free both his/her hands to flush the blocked cannula. This wastes valuable surgical time, reduces patient safety and surgical efficiency.

Referring to FIG. 1, when the peristaltic pump 4 rotates in direction 12, a negative pressure is created and transmitted to the tip 9 via the suction tube 5 and, in this manner, the liquid contents are successfully aspirated. However, blood clots could block the lumen 8 or the tip 9 and if such blocks are not relieved by flushing or by manually dislodging the clot from the tip 9, then the magnitude of the negative pressure inside the lumen of the suction tube 5 starts increasing, implying thereby that the vacuum pressure starts becoming more negative. The pressure inside the lumen 8 is always less than about the atmospheric pressure but, when a block occurs, the magnitude of the already existing negative pressure begins to increase steeply. This rising negative pressure is sensed by the pressure transducer 6 which in turn sends an appropriate signal via wires 14 to the controller 13. The controller can be so programmed when the pressure transducer 6 senses a steeply rising negative pressure the peristaltic pump 4 transiently rotates in the reverse direction 11 such that the clot is immediately flushed out of the lumen 8 or the clot is dislodged away from the tip 9.

Depending upon the surgical procedure and also the diameter of the lumen 8, there are many ways in which the controller could be programmed. Suitable input means are provided by which the controller could be programmed with respect to the operation of the pump 4 based on a pressure feedback mechanism. Some of the possible ways of programming the controller are discussed as follows by the help of hypothetical examples:

EXAMPLE 1

The surgeon first selects the flow rate at which the pump 4 would aspirate in the normal course by rotating in direction 12. Let it be assumed that in the normal course the pump 4 aspirates at about 50 ml/min. Let it also be assumed that the transducer 6 continuously senses a baseline negative pressure of minus 2 mm Hg while aspirating physiological fluids like normal saline and unclotted blood. Whenever the cannula gets blocked, the negative pressure starts rising steeply above the said baseline pressure of minus 2 mm Hg. The controller could be so programmed that immediately when the negative pressure starts to rise above the hypothetical value of minus 2 mm Hg the pump 4 rotates in the opposite direction 11 at any desired flow rate, for example at about 800 ml/min, for a short period of time, of about 3 seconds and subsequently the pump 4 again starts rotating in the same initial direction 12 at the same preselected flow rate of about 50 ml/min. The ideal reverse flow rate in direction 11 and corresponding ideal time duration could also be determined via experimental and clinical means for specific aspiration cannulas and specific surgeries. The possibility does exist that at the end of the said reverse motion 11 of the pump the clot is still not flushed out, and to deal with such a situation the controller could be alternatively programmed to continue moving the pump 4 in the reverse direction 11 until a release of a block is sensed in the form of a steep decline in the magnitude of the generated positive pressure and after this the pump could again start aspirating in direction 12 at the given hypothetical flow rate of about 50 ml/min.

When the pump momentarily moves in the reverse direction 11 at a high flow rate, the clot gets dislodged sufficiently away from the tip or the lumen of the cannula 7 and normal aspiration of water like fluids can continue subsequently. Such programming is useful in open surgical procedures of the abdomen wherein large volume of irrigation fluid instilled to wash a bleeding surgical site accumulates in the large recess of the abdominal cavity and this irrigation fluid needs to be aspirated. Multiple blood clots contained in the irrigation fluid tend to intermittently block the aspiration cannula, but with the method described in this paragraph the blood tinged irrigation fluid can be aspirated in an almost uninterrupted manner despite the blood clots which continuously tend to block the aspiration cannula. Such type of programming is useful only for aspirating liquids and not solids. The solid blood clots which are selectively left behind need to be mopped with a surgical towel or to be removed via other mechanical means. Such type of controller programming is also useful in laparoscopic procedures wherein the surgeon cannot manually dislodge a clot with the hand. However, such type of programming is not useful in brain surgery type of procedures where the main aim of surgical aspiration is to remove blood and blood clots from the surgical field, and not the irrigation fluid. If the described method is applied to brain surgery, the clots would keep falling back over the same spot on the surgical site, which offers no surgical benefit.

EXAMPLE 2

With respect to the programming described in the preceding paragraph, the controller could be additionally programmed such that whenever a blockage was detected in the form of a steeply rising negative pressure, the pump 4 was allowed to continue working in same direction 12 and at the same flow rate, which being the hypothetical value of about 50 ml/min in the present context, for a set time period, of about 5 seconds. If during these about 5 seconds the clot is successfully aspirated, the magnitude of the negative pressure falls to the said hypothetical value of minus 2 mm Hg and this could serve as a signal for the pump to continue working in the same direction 12 at the same hypothetical flow rate of minus 50 ml/min. While if at the end of these about 5 seconds the block is not removed, the negative pressure is not released and this could serve as a trigger for the pump to temporarily operate in the reverse direction 11 as already described in the previous paragraph. Such an arrangement gives a better chance for more clots to be successfully aspirated and the clots which are not successfully aspirated are again flushed back into the surgical site. During the about 5 seconds, the surgeon can move the tip 9 of the aspiration cannula out of the operating field so that the clots can be flushed or dropped out of the surgical field. The said time interval of 5 seconds could also be increased in case the surgeon so desired. Such type of controller programming is more beneficial in brain surgery procedures because such method allows the surgeon to dispose the blood clots outside the surgical field in a single handed manner. Such method also allows larger number of clots to be successfully aspirated. However, such method has the disadvantage that it does not provide a full chance to a clot to be successfully aspirated.

EXAMPLE 3

Via experimental and clinical means, an ideal negative pressure and an ideal time period could be derived which allows successful aspiration of most clots. Let it be assumed that a negative pressure of minus 7 mm Hg maintained for about 4 seconds allows successful aspiration of most clots. In accordance with this hypothetical teaching, the controller could be programmed so that subsequent to detecting a block in the form of a steeply rising negative pressure the pump 4 continues to work at the same flow rate or at some desired increased flow rate, in the same initial direction 12, until the negative pressure increased to the said hypothetical value of minus 7 mm Hg.

After the hypothetical pressure value of minus 7 mm Hg is attained, the pump 4 either completely stops or moves interruptedly at a very low RPM's such that minus 7 mm Hg pressure is maintained for the hypothetical time interval of about 4 seconds. During these about 4 seconds, all clots get the best chance to be successfully aspirated and any clot which is not successfully aspirated in these about 4 seconds can be deemed to be causing a permanent type of an obstruction. Also during these about 4 seconds, the surgeon can move the tip 9 of the aspiration cannula outside the surgical field such that the clots are finally flushed or disposed outside the surgical field, for example over the surgical drapes. At the end of these about 4 seconds, the flushing cycle and subsequent events continue as described in the previous paragraph. The time interval of about 4 seconds could also be increased in case the surgeon so desired. In most prior art systems, an uncontrolled negative pressure is created which could accidentally damage vital structures like small nerves and blood vessels during brain surgery type procedures. The method described in this paragraph limits the maximum negative pressure to minus 7 mm Hg. This negative pressure could be reduced to even a lesser value, of about 5 mm Hg and, in this manner, the present invention can also significantly enhance patient safety in brain surgery type of procedures.

Besides the three types of controller programming described above, the controller could be programmed in many more different ways depending upon surgical procedure and the lumen diameter of the aspiration cannula.

The flushing cycles described in the preceding paragraphs do not offer any risk to the sterile environment of the surgical field because each flushing cycle is capable of releasing only minute quantities fluid into the surgical field and this risk can also be further reduced by appropriate programming of the controller. However, to further safeguard against contamination of the surgical site two additional traps, a proximal trap 26 and a distal trap 22, are provided as shown in FIG. 5. These traps are optional and any number of traps (one or a plurality of traps) could be used.

Referring to FIG. 5, the proximal trap 26 may be a jar shaped container closed by an airtight lid 19. The suction tube 5 has been cut preferably near the pump 4 and two open ends of the suction tube are available. The opening of the suction tube 5 towards the aspiration cannula 7 is labeled 20, while the opening of the suction tube 5 towards the pump 4 is labeled 21. Both the cut ends of the suction tube enter the proximal trap 18 via the lid 19 such that air tight contact exists between both ends of the suction tube and the lid 19. The opening 20 is kept as high, that is as near to the lid 19 as possible, while the opening 21 is kept as close to the bottom of the proximal trap 18 as possible. Such arrangement is deliberately chosen so that minimum volume of the liquid and solid aspirate contents are present at any given time. Such arrangement protects against contamination of the surgical site when the pump 4 rotates in the reverse direction 11 during the flushing mode.

Again referring to FIG. 5, the distal trap 22 may be a jar shaped container closed by an airtight lid 23. The fluid drainage tube 2 has been cut preferably near the pump 4 and two open ends of the fluid drainage tube are available. The opening of the cut fluid drainage tube 2 towards the pump 4 is labeled 24, while the opening of the cut fluid drainage tube 2 towards the waste collecting container 1 is labeled 25. Both the cut ends of the fluid drainage tube 2 enter the distal trap 22 via the lid 23, such that air tight contact exists between both cut ends of the fluid drainage tube 2 and the lid 23. The opening 24 is kept as high as possible, that is as near to the lid 23 as possible, while the opening 25 is kept as close to the bottom of the distal trap 22 as possible. Such arrangement is deliberately chosen so that minimum volume of the liquid and solid aspirate contents are present at any given time. Such arrangement protects against contamination of the surgical site when the pump 4 rotates in the reverse direction 11 during the flushing mode.

The tube 10 leading to the pressure transducer 6 can get blocked by clots. Thus, the pressure transducer can also be connected to the proximal trap 26 in an appropriate manner.

Keeping human safety in mind, it is important that the present invention is meant to be used only in limited situations, such as (1) when a blood clot or tissue debris causes a permanent type of a block in the aspiration cannula, and such blocking clot/debris needs to be removed completely away from the surgical field, as in brain surgery; or (2) when a blood clot or tissue debris causes a permanent type of a block in the aspiration cannula, and such blocking clot/debris needs to be relocated from one part of the operating field to another part of the same operating field (e,g., the posterior abdominal wall in laparoscopic surgery). However, there are some absolute contraindications to the use of the present invention, one of the contraindication being aspiration during 'phakoemulsification procedure' performed in cataract surgery, and other similar procedures in which a debris/clot which causes a permanent type of a block in the aspiration cannula that cannot be totally removed from the surgical field by way of automatic retrograde flushing provided in the system of the present invention, and also in which it is not permitted to park the debris/clot at a different location in the surgical field (as is permitted in laparoscopic surgery). In phakoemulsification, the diseased cataract lens of the eye is broken by ultrasonic vibrations created by a metallic aspiration cannula; the fragmented lens pieces have to essentially pass via the lumen of the phako cannula; any fragmented lens pieces whose diameter is bigger than the lumen diameter of the phako cannula are further fragmented until they are able to pass through lumen of the phako cannula. If the present invention is used in procedures such as phakoemulsification, then a majority of the fragmented debris/lens pieces would not be aspirated, because each time a fragmented lens piece tended to block the tip of the aspiration cannula, then the same would be dislodged back into the anterior chamber of the eye by virtue of the automatic retrograde flushing provided in the system of the proposed invention. Thus, the present invention, if used in phacoemulsification procedure, could lead to permanent blindness in the eye.

In the present invention, a positive displacement, for example, a peristaltic pump, is preferred and a dynamic pump like a centrifugal pump is preferably not used. One important reason for such preference is that a peristaltic pump produces a flow which is pulsatile in nature and such pulsations facilitate complete aspiration of a relatively greater number of clot/debris pieces via the lumen of the aspiration cannula. In the present context, the pulsatile nature of the flow of the peristaltic pump can be compared with a situation in which the surgeon vigorously shakes the entire aspiration cannula in order to facilitate a relatively greater number of clot/debris pieces to be effectively aspirated through the lumen of the aspiration cannula. In the present invention, a pressure dampening device is preferably not attached to the aspiration cannula because a dampening device could significantly reduce the efficiency of the proposed invention by reducing the amplitude of the pulsations created by the positive displacement pump.

According to the present invention, the controller is used to operate the positive displacement pump so that at least one parameter of the operation of the positive displacement pump is controlled to a predetermined value. There may be a plurality of selectable predetermined values. The predetermined values may simply include "on" and "off". There may be user-interface means to allow the user to select at least one predetermined parameter. Preferably, more than one parameter of the pump operation is controlled. The parameter suitably comprises the rate of rotation of the pump. The pump direction may also be controlled. Preferably, both the pump direction and the rate of rotation of the pump are controlled.

The controller may comprise sensing means for determining at least one parameter of operation of the pump. For example, a pressure transducer may be provided for sensing the pressure in the suction tube.

Again keeping human safety in mind, it is important to reiterate that in the present invention at least one parameter of operation, suitably the RPM and the direction of rotation of the peristaltic pump, is always regulated by the controller and never by a human operator. A human operator controlling the peristaltic pump in any manner could prove dangerous for the patient. In some surgeries, like brain surgery, the aspiration system is in the 'switch on' position all through the surgery, while in surgeries like laparoscopic surgery, the aspiration system is switched on only when required. A footswitch is often used to switch on or to switch off a surgical aspiration system.

In many prior art aspiration systems, such as aspiration systems used in phakoemulsification surgery, the surgeon directly regulates the RPM of aspiration peristaltic pump by pressing up or down on the foot switch; in such case the wires from the footswitch often pass through a controller, but the controller does not participate in regulating the peristaltic pump as is the case in the present invention.

Keeping in mind the surgical efficiency and surgeon's comfort, audio signals of varying amplitude and or frequency could also be provided in the system of the proposed invention. Such audio signals could be related to actions such as a clot blocking the aspiration cannula in a permanent like manner or when the pump runs in the reverse direction 11 to flush out a clot. An audio signal could also be related to a situation wherein a clot/debris is successfully aspirated through the aspiration cannula. Such audio signals would continuously inform the surgeon as to what the controller is doing.

There is no other known system in which the surgeon can aspirate a surgical site by constantly holding the aspiration cannula in the same hand. Thereby, the other hand of the surgeon is never used for managing or manipulating the aspiration system in any manner. Also there is no prior art system by which a surgical site could be aspirated in an almost uninterrupted manner, preferably in an uninterrupted manner, despite blood clots and tissue debris which constantly block the tip or the lumen of the aspiration cannula.

The present invention allows the surgeon to aspirate a surgical site single handedly in an uninterrupted manner despite blood clots and tissue debris which intermittently block the tip or the lumen of the aspiration cannula. The invention makes surgical aspiration safe, simple, more accurate, and easy to perform. The advantages of the present invention are summarized in the following table along with the corresponding disadvantages of the prior art systems:

In conclusion, the present invention provides a safe and efficient surgical aspiration system and method. The system can be used single handedly and can aspirate a surgical site in an uninterrupted manner, despite blood clots and tissue debris which constantly block the tip or the lumen of the aspiration cannula. The system is useful in many open surgical procedures and in operative laparoscopic procedures. However, the invention is especially useful in brain surgery where surgical aspiration plays a critically vital role. The system can substantially reduce the total operating time, can significantly enhance patient safety, and can increase surgical efficiency in brain surgery and other related procedures. Thus the invention is extremely useful for entire mankind.

Although the present invention has been described in connection with preferred embodiments, many modifications and variations will become apparent to those skilled in the art. While preferred embodiments of the invention have been described and illustrated above, it should be understood that these are exemplary of the invention and are not to be considered as limiting. Accordingly, it is not intended that the present invention be limited to the illustrated embodiments, but only by the appended claims.

What is claimed as new and desired to be protected by Letters Patent of the United States is:

1. A surgical aspiration system, comprising:
    a suction tube connected to an aspiration cannula and in the vicinity of a surgical site for removing blood, blood clots and tissue debris from the surgical site without irrigation of the surgical site;
    a controller configured to detect pressure variations in the suction tube caused by blockage of blood clot or tissue debris in at least a portion of the suction tube and in response generating an output signal;
    a positive displacement pump connected to the suction tube, the positive displacement pump being further directly connected to the controller for receiving therefrom the output signal that operates the positive displacement pump based on the sensed pressure variations; and
    a first airtight container in communication with an end of the suction tube.

2. The surgical aspiration system of claim 1, further comprising a pressure transducer connected to the suction tube for sensing the pressure in the suction tube.

3. The surgical aspiration system of claim 1, wherein the controller operates the positive displacement pump in a direction different from the direction in which the fluid is suctioned through the suction tube.

| ADVANTAGES OF THE SURGICAL ASPIRATION SYSTEM OF THE PRESENT INVENTION | DISADVANTAGES OF THE PRIOR ART SYSTEMS |
|---|---|
| The surgeon or the assistant never uses his/her other hand to dislodge or to flush out a clot which blocks the tip or the lumen of the aspiration cannula | This is not possible in any prior art system |
| The blockage of the aspiration cannula caused by clots and debris is relieved automatically | This is not possible in any prior art system |
| The blockage of the aspiration cannula caused by clots and debris is relieved automatically after a desired time lag period | This is not possible in any prior art system |
| The system can aspirate in an uninterrupted manner despite blood clots and tissue debris which constantly block the tip or the lumen of the aspiration cannula | This is not possible in any prior art system |

4. The surgical aspiration system of claim 1, wherein the positive displacement pump is selected from the group consisting of peristaltic pump, piston pump, gear pump and diaphragm pump.

5. The surgical aspiration system of claim 4, wherein the positive displacement pump is a peristaltic pump.

6. The surgical aspiration system of claim 1, further comprising a second airtight container in communication with another end of the suction tube.

7. The surgical aspiration system of claim 1, wherein the surgical site is a laproscopic site or a neurosurgical site.

8. The surgical aspiration system of claim 1, wherein the surgical site is the brain.

9. A single-handed aspiration system for aspirating blood, blood clots and tissue debris uninterruptedly, comprising:
- a suction tube connected to an aspiration cannula and in the vicinity of a surgical site for removing blood, blood clots and tissue debris from the surgical site in a first direction and without irrigation of the surgical site;
- a peristaltic pump connected to the suction tube;
- a pressure transducer connected to the suction tube and configured to generate pressure signals indicative of a difference in pressure in the suction tube; and
- a controller connected to the pressure transducer for receiving pressure signals therefrom and being further connected to the peristaltic pump for operating the peristaltic pump uninterruptedly in response to the pressure signals from the pressure transducer, and for aspirating the blood, blood clots and tissue debris uninterruptedly.

10. The aspiration system of claim 9, wherein the pressure transducer generates pressure signals when blood clots or tissue debris block at least a portion of the suction tube.

11. The aspiration system of claim 10, wherein the controller operates the peristaltic pump in a direction which is opposite the first direction.

12. The aspiration system of claim 9, wherein the suction tube has a diameter of at least 0.3 mm.

13. The aspiration system of claim 9, wherein the surgical site is a laproscopic site or a neurosurgical site.

14. The aspiration system of claim 9, wherein the surgical site is the brain.

* * * * *